United States Patent [19]

Massingill

[11] 4,313,886
[45] Feb. 2, 1982

[54] PROCESS FOR PREPARING LIQUID EPOXY RESINS

[75] Inventor: John L. Massingill, Lake Jackson, Tex.

[73] Assignee: The Dow Chemical Company, Midland, Mich.

[21] Appl. No.: 190,700

[22] Filed: Sep. 25, 1980

[51] Int. Cl.$^3$ .......................................... C07D 301/28
[52] U.S. Cl. ............................................... 260/348.15
[58] Field of Search .................................... 260/348.15

[56] References Cited

U.S. PATENT DOCUMENTS

| | | | |
|---|---|---|---|
| 2,943,095 | 6/1960 | Farnham et al. | 260/348.15 |
| 2,943,096 | 6/1960 | Reinking | 260/348.15 |
| 2,986,551 | 5/1961 | Griffin et al. | 260/348.15 |
| 2,995,583 | 8/1961 | Larkin et al. | 260/348.15 |
| 3,023,225 | 2/1962 | Reinking | 260/348.15 |
| 3,129,232 | 4/1964 | Terford et al. | 260/348.15 |
| 3,176,027 | 3/1965 | Budnowski et al. | 260/348.15 |
| 3,221,032 | 11/1965 | Price et al. | 260/348.15 |
| 3,352,825 | 11/1965 | Price | 260/47 |
| 3,413,320 | 11/1968 | Cofer | 260/348 |
| 3,767,618 | 10/1973 | Hairston et al. | 260/348.15 |
| 3,980,679 | 9/1976 | Becker | 260/348.15 |
| 4,017,523 | 4/1977 | Variu et al. | 260/348.15 |

FOREIGN PATENT DOCUMENTS

| | | | |
|---|---|---|---|
| 1133735 | 7/1962 | Fed. Rep. of Germany | 260/348.15 |
| 843575 | 8/1960 | United Kingdom | 260/348.15 |
| 1159530 | 7/1969 | United Kingdom | 260/348.15 |

OTHER PUBLICATIONS

A. Weissberger, Heterocyclic Compounds with Three- and Four-Membered Rings, Part One (1964), pp. 310-311.

Primary Examiner—Norma S. Milestone
Attorney, Agent, or Firm—J. G. Carter

[57] ABSTRACT

Liquid epoxy resins are produced by reacting an epihalohydrin and a dihydric phenol in the presence of a catalyst in a multistage reaction wherein between each stage the excess epihalohydrin and glycerin dihalohydrin by-product are removed and epihalohydrin is added to the subsequent reactor.

4 Claims, No Drawings

PROCESS FOR PREPARING LIQUID EPOXY RESINS

BACKGROUND OF THE INVENTION

Liquid epoxy resins are usually prepared by reacting an epihalohydrin and a dihydric phenol in the presence of a catalyst to produce a halohydrin-containing resin intermediate and thereafter reacting such intermediate with a basic acting material such as sodium hydroxide. The resultant reaction mixture is then treated, usually by water washing, to remove salt and residual catalyst.

The present process does not employ any basic acting material thereby producing a salt free reaction mixture which provides a water washing stream free of such salt which provides for easier recovery of catalyst, if desired, or easier waste disposal since the salt free water wash stream effluent does not have to be diluted prior to being sent to biotreatment waste disposal means.

SUMMARY OF THE INVENTION

The present invention provides a process for preparing liquid diglycidyl ethers of dihydric phenols which process comprises (A) reacting in a first reactor in the presence of a suitable quantity of a suitable catalyst an epihalohydrin or mixture of epihalohydrins with a dihydric phenol or mixture of dihydric phenols in a molar ratio of epihalohydrin to dihydric phenol of from about 5:1 to about 20:1, preferably from about 8:1 to about 12:1 for a time amounting to about 90 to 110%, preferably 95 to 105% of the time required for the reaction mixture to reach equilibrium;

(B) subjecting the reaction mixture produced in said first reactor to flash distillation so as to remove epihalohydrin and glycerin dihalohydrin therefrom;

(C) contacting the distilland from step (B) in a subsequent reactor in the presence of a suitable catalyst with an epihalohydrin in a weight ratio of epihalohydrin to distilland of from about 1:1 to about 20:1, preferably from about 3:1 to about 6:1 for a time amounting to about 90 to 110%, preferably 95 to 105% of the time required for the reaction mixture to reach equilibrium;

(D) repeating steps (B) and (C) until the distilland contains less than about 1000 ppm, preferably less than about 500 ppm, most preferably about 300 ppm hydrolyzable halide; and (E) thereafer removing any residual quantities of catalyst therefrom.

DESCRIPTION OF THE PREFERRED EMBODIMENTS

Suitable dihydric phenols which can be employed herein include, for example, hydroquinone, resorcinol, catechol, and bisphenols such as those represented by the formula

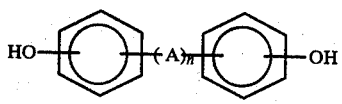

wherein A is a divalent hydrocarbon group having from 1 to about 10 carbon atoms, —S—, —S—S—,

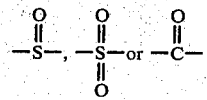

and n has a value of zero or 1, mixtures thereof and the like.

Suitable epihalohydrins which can be employed herein include, for example, epichlorohydrin, epibromohydrin, epiiodohydrin, methylepichlorohydrin, methylepibromohydrin, methylepiiodohydrin, mixtures thereof and the like.

Suitable catalysts include, for example, quaternary ammonium compounds, quaternary phosphonium compounds, sulfonium compounds and the like.

Suitable quaternary ammonium catalysts include, for example, tetramethyl ammonium chloride, benzyl trimethyl ammonium chloride, triethanol ammonium chloride, tetraethanol ammonium hydroxide, dodecyl dimethylbenzyl ammonium naphthenate and the like.

Suitabe quaternary phosphonium catalysts include, for example, those quaternary phosphonium compounds disclosed in U.S. Pat. Nos. 3,948,855, 3,477,990 and 3,341,580 and Canadian 858,648 all of which are incorporated herein by reference. Particularly suitable such catalysts include, for example, ethyl triphenyl phosphonium iodide, ethyl triphenyl phosphonium bicarbonate, ethyl triphenyl phosphonium acetate.acetic acid complex, benzyl triphenyl phosphonium chloride, tetrabutyl phosphonium chloride, benzyl trimethyl ammonium chloride mixtures thereof and the like.

Suitable sulfonium catalysts include thiourea catalysts such as, for example, tetramethyl thiourea; N,N'-dimethyl thiourea; N,N'-diphenyl thiourea; mixtures thereof and the like as well as thiodiethanol and other sulfonium precursors.

Also suitable as catalysts are the basic ion exchange resins such as, for example, DOWEX MSA-1, DOWEX 11, DOWEX SBR, mixtures thereof and the like.

The reaction temperature is not critical so long as the temperature is below that which would destroy the activity of the particular catalyst employed. Suitable temperatures for conducting the reaction between epihalohydrin and dihydric phenol are from about 25° C. to about 180° C., preferably from 45° C. to about 150° C. Any pressure is suitable so long as it will maintain an excess of epihalohydrin to dihydric phenol in the liquid phase at the particular temperature employed.

The time required for reaching equilibrium can readily be ascertained by contacting small portions of the reactants in the ratios to be employed and at the reaction conditions to be employed and periodically analyzing for glycerin dihalohydrin and when such analysis appears to be constant then it is assumed that an equilibrium has been reached.

The quantity of hydrolyzable halide present in the distill and can readily be ascertained by hydrolysis and titration as described in ASTM D-1726.

The flash distillation can be accomplished by any suitable method such as, for example, falling film stills, or wiping film stills, so long as the conditions are such as to remove at least about 90 percent, preferably at least about 95 percent of the glycerine dihalohydrin from the reactor effluent.

The distillate containing epihalohydrin and glycerin dihalohydrin can be subsequently subjected to separation by solvent extraction or fractional distillation and the epihalohydrin recycled in the process and the glycerin dihalohydrin converted to epihalohydrin by suitable means.

The following examples are illustrative to the invention, but are not to be construed as to limiting the scope thereof in any manner.

EXAMPLE 1

Epichlorohydrin and bisphenol A (10:1 molar ratio) was mixed with 0.42 weight percent of catalyst solution (60% benzyltrimethyl ammonium chloride in water) and heated for 5 days at 42° C. to 70° C. The resulting coupled mix (30 cc), containing 13.2% glycerin dichlorohydrin (GDCH), was evaporated on a rotary vacuum evaporator to obtain the resin intermediate (10 grams). This intermediate was mixed with 30 grams of epichlorohydrin and equilibrated at 60° C. for 8 hours to give a mix containing 4.7% GDCH. The evaporation procedure was repeated and the resulting resin intermediate was mixed with 60 grams of epichlorohydrin and equilibrated at 60° C. for 4 hours to give a mix containing 1.7% GDCH. The evaporation procedure was repeated and the resulting resin intermediate was again mixed with 60 grams of epichlorohydrin and equilibrated at 60° C. for 4 hours to give a mix containing 0.4% GDCH. Table I shows the resin analysis of each equilibrium stage.

TABLE I

| ANALYSIS OF RESIN AFTER EACH EQUILIBRIUM STAGE | | | | |
|---|---|---|---|---|
| Stage | 1 | 2 | 3 | 4 |
| Epi/Resin Wt. Ratio | 2/1 | 3/1 | 6/1 | 6/1 |
| % Resin | 32.4 | 75 | 90.5 | 99.5 |
| % Monochlorohydrin Resin | 37.9 | 25 | 9.5 | trace |
| % Dichlorohydrin Resin | 27.5 | nil | nil | nil |
| % Hydrolyzable Chloride | 7.2 | 2.6 | 0.9 | <0.05 |
| % Epoxidation | 59.3 | 84.9 | 94.8 | >99.7 |

EXAMPLE 2

Another reaction similar to example 1, except using larger quantities of reactants and using 5 equilibration stages, produced a resin with the following physical properties:

| % hydrolyzable chloride | 220 ppm |
|---|---|
| Viscosity | 10,530 cps @ 25° C. |

I claim:
1. A process for preparing liquid diglycidyl ethers of dihydric phenols which process comprises:
   (A) reacting in a first reactor in the presence of a suitable quantity of a suitable catalyst selected from quaternary ammonium compounds, quaternary phosphonium compounds, sulfonium compounds, basic ion exchange resins and mixtures thereof, an epihalohydrin or mixture of epihalohydrins with a dihydric phenol or mixture of dihydric phenols in a molar ratio of epihalohydrin to dihydric phenol of from about 5:1 to about 20:1 for a time amounting to from about 90% to about 110% of the time required for the reaction mixture to reach equilibrium;
   (B) subjecting the reaction mixture produced in said first reactor to flash distillation so as to remove epihalohydrin and glycerin dihalohydrin therefrom;
   (C) contacting the distllland from step (B) in a subsequent reactor in the presence of a suitable catalyst as aforementioned with an epihalohydrin in a weight ratio of epihalohydrin to distilland of from about 1:1 to about 20:1 for a time amounting to from about 90% to about 110% of the time required for the reaction mixture to reach equilibrium;
   (D) repeating steps (B) and (C) until the distilland contains less than about 1000 ppm, hydrolyzable halide; and
   (E) thereafter removing any residual quantities of catalyst therefrom.

2. The process of claim 1 wherein (1) in steps (A) and (C), the contact time is from about 95% to about 105% of the time required for the reaction to reach equilibrium and (2) in step (D), the distilland contains less than about 500 ppm hydrolyzable halide.

3. The process of claim 2 wherein (1) in step (D), the distilland contains less than about 300 ppm hydrolyzable halide and (2) step (E) is accomplished by water washing the finished resin.

4. The process of claims 1, 2 or 3 wherein said epihalohydrin is epichlorohydrin and said dihydric phenol is bisphenol A.

* * * * *

UNITED STATES PATENT AND TRADEMARK OFFICE
CERTIFICATE OF CORRECTION

PATENT NO. : 4,313,886
DATED : February 2, 1982
INVENTOR(S) : John L. Massingill It is certified that error appears in the above—identified patent and that said Letters Patent is hereby corrected as shown below:

In the references cited, page 1, correct the date for Patent No. 3,352,825 from "11/1965" to --11/1967--.

Col. 1, line 51, correct "thereafer" to --thereafter--.

Col. 2, line 23, correct "Suitabe" to --Suitable--.

Col. 2, line 48, please add --about-- before "45°C".

Col. 2, line 60, correct "distill and" to --distilland--.

Col. 4, (Claim 1) line 26, correct "distllland" to --distilland--.

Signed and Sealed this

Sixth Day of July 1982

[SEAL]

Attest:

GERALD J. MOSSINGHOFF

Attesting Officer

Commissioner of Patents and Trademarks